(12) United States Patent
Sufyan et al.

(10) Patent No.: US 10,485,645 B2
(45) Date of Patent: Nov. 26, 2019

(54) STRESS URINARY INCONTINENCE TREATMENT MEDICAL IMPLANT

(71) Applicant: IPENGINE MANAGEMENT (INDIA) PRIVATE LIMITED, New Delhi (IN)

(72) Inventors: Mohammad Sufyan, New Delhi (IN); Rajeev Malhotra, Newton, MA (US); Lee Richstone, New York, NY (US); Manish Vira, New York, NY (US)

(73) Assignee: IPENGINE MANAGEMENT (INDIA) PRIVATE LIMITED, New Delhi (IN)

( * ) Notice: Subject to any disclaimer, the term of this patent is extended or adjusted under 35 U.S.C. 154(b) by 166 days.

(21) Appl. No.: 15/322,159

(22) PCT Filed: Jun. 25, 2015

(86) PCT No.: PCT/IN2015/050054
§ 371 (c)(1),
(2) Date: Dec. 26, 2016

(87) PCT Pub. No.: WO2015/198355
PCT Pub. Date: Dec. 30, 2015

(65) Prior Publication Data
US 2017/0151047 A1    Jun. 1, 2017

(30) Foreign Application Priority Data

Jun. 26, 2014 (IN) .......................... 1714/DEL/2014

(51) Int. Cl.
*A61F 2/00* (2006.01)

(52) U.S. Cl.
CPC .... *A61F 2/0045* (2013.01); *A61F 2220/0008* (2013.01); *A61F 2220/0016* (2013.01); *A61F 2230/006* (2013.01); *A61F 2250/0003* (2013.01)

(58) Field of Classification Search
CPC .................. A61F 2/0045; A61F 2/0063; A61F 2220/0016
See application file for complete search history.

(56) References Cited

U.S. PATENT DOCUMENTS

2011/0112357 A1*   5/2011   Chapman ........... A61B 17/0401
                                                               600/37
2012/0296345 A1*   11/2012   Wack ................. A61B 17/0483
                                                               606/139

(Continued)

*Primary Examiner* — Thaddeus B Cox
(74) *Attorney, Agent, or Firm* — Sheets Law Office; Kendal Sheets

(57) ABSTRACT

The present invention provides an implant that includes inflatable anchors that are configured to assume an inflated state and a relaxed state. The implant includes a tubular member mechanically coupled to one or more anchors of the inflatable anchors. The tubular member includes a lumen that provides a passageway for circulating a fluid through the one or more of the plurality of inflatable anchors and allow them to protrude and pierce through bodily tissues. In an embodiment, the implant may include a plurality of bi-directional barbs instead of the inflatable anchors. The plurality of barbs may be activated by a flexible member such that the activation is configured to cause anchoring of the barbs into soft tissues during a surgical procedure. The present invention provides a method for placing an implant. The method includes delivering the implant inside a body along a pathway through an opening proximate sacrum and attaching a first portion of the implant to an anterior vaginal wall, attaching a second portion of the implant to a posterior vaginal wall and attaching a third portion of the implant to a tissue proximate the sacrum.

6 Claims, 15 Drawing Sheets

(56) References Cited

U.S. PATENT DOCUMENTS

| | | | | |
|---|---|---|---|---|
| 2013/0109910 A1* | 5/2013 | Alexander | ....... | A61B 17/00234 600/37 |
| 2013/0204277 A1* | 8/2013 | Fabry | ................. | A61B 17/0057 606/151 |
| 2013/0303840 A1* | 11/2013 | Goldman | .............. | A61F 2/0045 600/30 |
| 2014/0094829 A1* | 4/2014 | Kostrzewski | ......... | A61F 2/0063 606/151 |

* cited by examiner

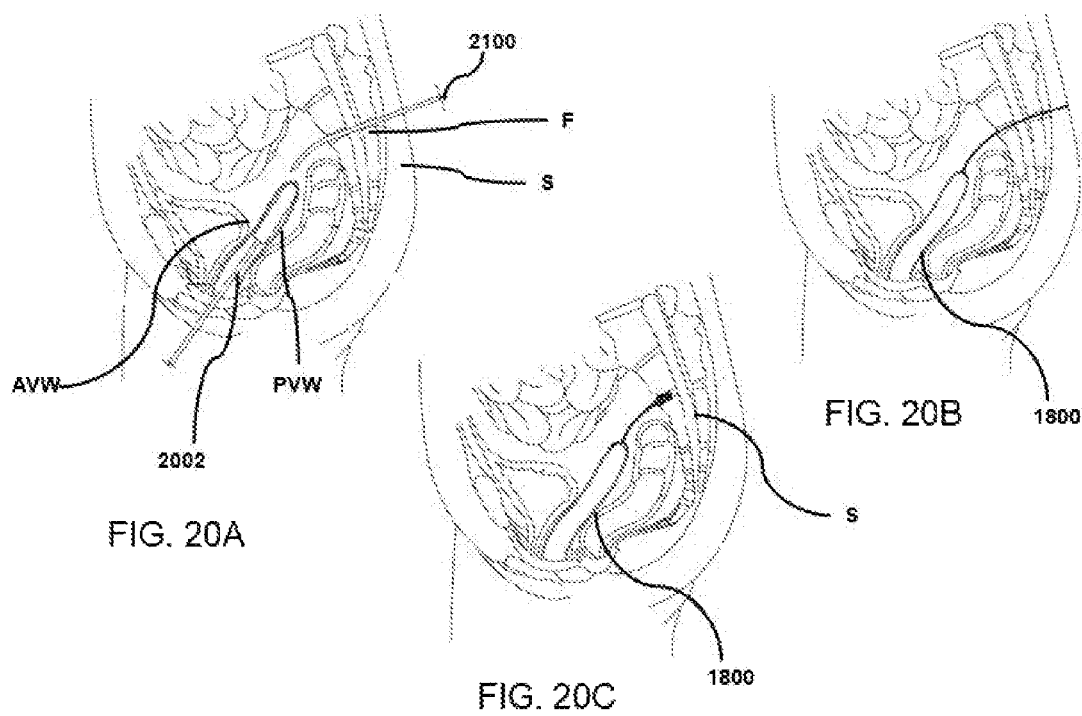

STRESS URINARY INCONTINENCE TREATMENT MEDICAL IMPLANT

BACKGROUND

Field

The present invention generally relates to medical implants and more particularly relates to delivery, positioning, and fixation of the medical implants in a patient's body, and methods and systems thereof.

Description of the Related Art

Pelvic health for men and women is a medical area of increasing importance due to an aging population. Examples of common pelvic ailments include fecal incontinence, urinary incontinence, pelvic tissue prolapse e.g., vaginal wall prolapse, and other disorders of the pelvic floor.

Current treatment options include dietary and lifestyle changes and exercises to strengthen the pelvic muscles (Kegels), use of a pessary, and surgical procedures. Various kinds of surgical methods are used for treating pelvic organ prolapse and incontinence. These procedures may include, for example, sub-urethral support, support to bladder neck, vaginal wall or vaginal vault prolapse surgery, cystocele surgery, urethrocele surgery, rectocele surgery, enterocele surgery, and hysterectomy, and the like. During vaginal wall surgery for example, a surgeon usually makes incisions in the walls of the vagina and then tries to reattach support tissues to their original positions. This can be difficult and dangerous and is quite often unsuccessful. As a result various prosthetic meshes have been developed in an attempt to more strongly compensate for the damage of the native tissue and the inability to recreate the original support. Further, fixation of a surgical implant for use in incontinence repair or prolapse repair may also be a complicated task and requires extreme care.

In view of the above, there is a need for an improved procedure for repairing pelvic disorders and providing improved ways and devices for delivering, placing, and attaching implants inside a body of a patient.

SUMMARY

The present invention provides an implant for providing support to a weakened tissue. The implant includes an elongate body member with a proximal portion, a distal and an intermediate portion. The intermediate portion is configured to be positioned proximate the weakened tissue underneath urethra to provide support. The implant further includes a plurality of inflatable anchors positioned on an outer surface of the elongated body member. The plurality of inflatable anchors are configured to assume an inflated state and a relaxed state. The implant further includes a tubular member mechanically coupled to one or more anchors of the plurality of inflatable anchors. The tubular member includes a lumen that provides a passageway for circulating a fluid through the one or more anchors of the plurality of inflatable anchors. The implant may include an injection port coupled to the tubular member for injecting the fluid.

The present invention provides a method for placement and fixation of an implant to support a weakened tissue. The method includes delivering the implant inside a body of a patient. The implant includes an elongate body member and a plurality of inflatable anchors positioned on an outer surface of the elongated body member, wherein the plurality of inflatable anchors are configured to assume an inflated state and a relaxed state. The method includes placing the implant at a target site underneath the weakened tissue. The method further includes injecting a fluid through a tubular member mechanically coupled to the plurality of inflatable anchors so as to cause inflation of the inflatable anchors, wherein the inflation facilitates piercing of the plurality of inflatable anchors within bodily tissues and fixation of the implant at the target site.

The present invention provides an implant for providing support to a weakened tissue. The implant includes a first strip, a second strip and a third strip coupled together to define a Y-shaped sling. The Y-shaped sling is configured to provide support to vaginal walls for treatment of vaginal wall prolapse. The first strip is configured to be attached to an anterior vaginal wall, the second strip is configured to be attached to a posterior vaginal wall, and the third strip is configured to be attached proximate sacrum. The implant further includes a plurality of inflatable anchors positioned on an outer surface of the first strip such that the plurality of inflatable anchors are configured to assume an inflated state and a relaxed state. The implant includes a tubular member mechanically coupled to one or more anchors of the plurality of inflatable anchors, wherein the tubular member includes a lumen that provides a passageway for circulating a fluid through the one or more anchors of the plurality of inflatable anchors. The implant may further include an injection port coupled to the tubular member for injecting the fluid.

The present invention provides an implant for treatment of stress urinary incontinence. The implant includes an elongate body member with a proximal portion, a distal portion, and an intermediate portion, wherein the intermediate portion is configured to be positioned proximate a weakened tissue underneath urethra to provide support. The implant further includes a plurality of bi-directional barbs positioned on an outer surface of the elongated body member. The plurality of bi-directional barbs may include a first set of barbs directed to a first direction and disposed proximate the proximal portion and a second set of barbs directed to a second direction and disposed proximate the distal end portion. The plurality of bi-directional barbs are configured to assume an exposed state and a relaxed state. The implant further includes a first flexible member attaching to at least one barb of the first set of barbs, and a second flexible member attaching to at least one barb of the second set of barbs. The first flexible member and the second flexible member are configured to cause the at least one barb of the first set of barbs and the at least one barb of the second set of barbs respectively to assume the exposed state from the relaxed state upon activation such that the activation is configured to cause anchoring of the exposed barbs into soft tissues during a surgical implant of the implant.

The present invention provides a method for fixation of a urogynecoloical implant with bodily tissues underneath urethra for urinary incontinence treatment. The method may include delivering the implant inside a body of a patient, wherein the implant includes an elongate body member and a plurality of bi-directional barbs disposed on an outer surface of the elongate body member. The plurality of bi-directional barbs may include a first set of barbs directed to a first direction and a second set of barbs directed to a second direction. The implant may include a first flexible member attaching to at least one barb of the first set of barbs, and a second flexible member attaching to at least one barb of the second set of barbs. The method may include placing the implant at a target site underneath the urethra so that an intermediate portion of the elongate body member supports the urethra and end portions of the elongate body member along with the first flexible member and the second flexible extend out of the body through two contra lateral abdominal incisions. The method may include pulling ends of the first flexible member and the second flexible member on either sides of the implant through the two abdominal incisions so as to actuate the at least one barb of the first set of barbs and the at least one barb of the second set of barbs associated with the first flexible member and the second flexible member respectively. The actuation causes the at least one barb of the first set of barbs and the at least one barb of the second set of barbs to get exposed and penetrate through bodily tissues for fixation of the implant. The method may include cutting end portions of the first flexible member and the second flexible member that hang outside the body, after fixation.

The present invention provides a method for placing an implant for vaginal wall prolapse treatment. The method includes delivering the implant inside a body along a pathway through an opening proximate sacrum. The method may include attaching a first portion of the implant to an anterior vaginal wall and attaching a second portion of the implant to a posterior vaginal wall and attaching a third portion of the implant to a tissue proximate the sacrum.

BRIEF DESCRIPTION OF THE FIGURES

The invention and the following detailed description of certain embodiments thereof may be understood with reference to the following figures:

FIGS. 20A-20C illustrate delivery and positioning of an implant inside a body of a patient in accordance with an embodiment of the present invention.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The terms "a" or "an," as used herein, are defined as one or more than one. The term "another," as used herein, is defined as at least a second or more. The terms "including" and/or "having", as used herein, are defined as comprising (i.e., open transition).

The embodiments of the present invention may be implemented in slings suitable for the treatment of urinary incontinence, faecal incontinence and to effect pelvic floor, perineal floor, and pelvic proplapse repairs.

Figure 1:
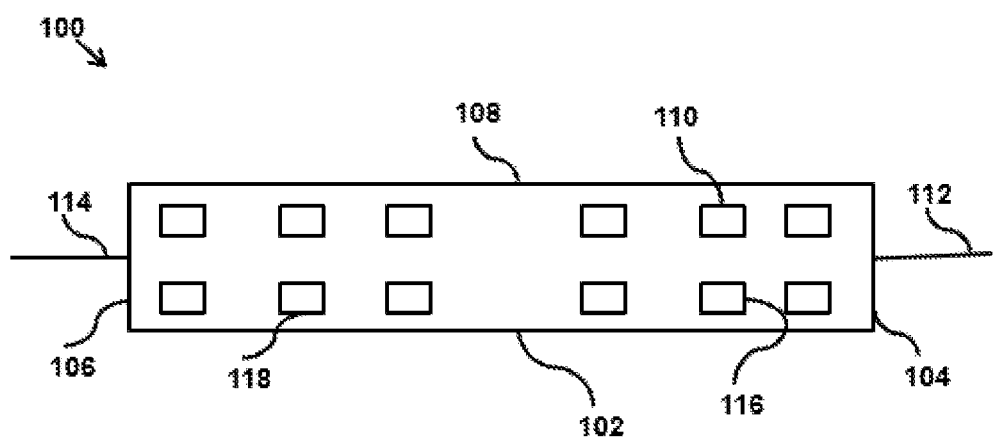
FIG. 1 illustrates a schematic diagram of an implant in accordance with an embodiment of the present invention.

FIG. 1 illustrates a block diagram of an implant 100 for use in the treatment of pelvic floor disorders such as but not limited to urinary incontinence, anterior vaginal wall prolapse, posterior vaginal wall prolapse, apical prolapse, or any other organ or tissue prolapse. In some embodiments, the implant 100 may be used to treat hernia. In other embodiments, the implant 100 may be used to treat any other weakened organ or tissues in a patient's body. The implant 100 includes an elongate body member 102. The elongate body member 102 includes a proximal end portion 104 and a distal end portion 106. The proximal end portion 104 and the distal end portion 106 of the implant 100 may be adapted to be fixed to bodily locations so as to support an organ or a weakened tissue. The implant 100 includes an intermediate portion 108 that may be positioned proximate a weakened tissue to be supported by the implant 100. For example, in an embodiment when the implant 100 is used for the treatment of urinary incontinence, the intermediate portion 108 also referred to as support portion 108 may be positioned underneath urethra for providing support to the urethra and the proximal end portion 104 and the distal end portion 106 may be attached to bodily tissues on either sides of the urethra to fix the implant 100 appropriately.

The length and width of the implant 100 may be defined based on anatomical structure of a patient and a target location. In an embodiment, the width of the implant 100 may be kept uniform from the proximal end portion 104 to the distal end portion 106. In an embodiment, the width of the implant 100 may vary. For example, the support portion 108 may be defined with increased width to support the target tissue and the proximal and distal end portions 104 and 106 may be defined with relatively reduced width. In an embodiment, the implant 100 may be symmetrically shaped about both longitudinal axis and its transverse axis. In another embodiment, the implant 100 may not be symmetric about at least one of the longitudinal axis and the transverse axis.

In an embodiment, the implant 100 generally defines an elongated portion wherein the intermediate support portion 108 may define a hexagonal, rectangular, linear, triangular or any other shape. In an embodiment, the implant 100 can be a linear strip of a mesh or non-mesh based material. In some embodiments, the end portions (proximal end portion 104 and the distal end portion 106) are made of same material. In some embodiments, the proximal end portion 104, the distal end portion 106, and the intermediate portion 108 may be made of one or more materials. In some embodiments, various portions of the implant 100 may be made of synthetic material or biologic material or a combination thereof. In some embodiments, the implant 100 may include polymeric material with or without mesh cell structures. Exemplary polymeric materials are polypropylene, polyester, polyethylene, nylon, PVC, polystyrene, and the like. In some embodiments, the implant 100 is made of a non-woven polymeric material. In an embodiment, the implant 100 is made of a woven material. In an embodiment, the constituent material is knit to form the implant 100. The implant 100 may be defined in the form of a mesh that may be made from a monofilament. In an example, the mesh implant 100 can be made from coated or uncoated monofilament macro-porous polypropylene. In an example, the surface of the mesh is smooth to avoid or reduce irritation on adjacent body tissues during interactions with bodily tissues. In an example, the mesh is stretchable and flexible to adapt movements along an anatomy of the patient body and reduce suture pullout. In some embodiments, the implant 100 can be made from natural materials such as biologic materials or cadaveric tissues. Exemplary biologic materials can be bovine dermis, porcine dermis, porcine intestinal sub mucosa, bovine pericardium, a cellulose based product, cadaveric dermis, and the like. In some embodiments, the implant 100 may be made from a biodegradable or a bio-absorbable material. In some embodiments, the implant 100 may be made from any other biocompatible material.

The implant 100 includes a plurality of barbs 110 (hereafter interchangeably referred to as barbs 110) that are located at distinct locations on the implant 100. In an embodiment, the barbs 110 are positioned on the proximal and distal end portions 104 and 106 of the implant 100. In an embodiment, the barbs 110 are positioned on the support portion 108 as well. In an embodiment, the barbs 110 are unidirectional in nature. In an embodiment, the barbs 110 are bi-directional in nature with one sided barbs disposed on a first portion of the implant 100 and substantially opposite sided barbs disposed on a second portion of the implant 100. For example, a first set of barbs 116 disposed on the first portion of the implant 100 may be directed toward a first direction and a second set of barbs 118 disposed on the second portion of the implant 100 may be directed toward a second direction. In some embodiments, orientations or directions of the barbs 110 may be along a longitudinal axis or substantially along the longitudinal axis of the implant 100. In some embodiments, the orientations or directions of the barbs 110 may not be substantially along the longitudinal axis of the implant 100. In some embodiments, the orientations of the different barbs 110 may be different based on fixation requirements.

Each of the barbs 110 may include a pointed tip portion that is adapted to pierce bodily tissues for fixation. The barbs 110 include base portions that extend from the implant 100. In embodiments, the barbs 110 are configured on outer surface of the implant 100. In an embodiment, the barbs 110 are configured on an entire outer surface. In an embodiment, the barbs 110 are configured on a selected portion of the outer surface. The base portions of the barbs 110 are coupled to the outer surface of the implant 100 so that the barbs 110 are movable with respect to the outer surface of the implant 100 in an embodiment. For example, the barbs 110 can rotate with respect to the outer surface. In an embodiment, the base portions of the barbs 110 may include holes through which implant 100 fibres may extend so as to couple the barbs 110 with the elongate body member 102 in a manner that would allow movement of the barbs 110 with respect to the outer surface of the implant 100 or body of the implant 100. In an embodiment, the base portions of the barbs 110 may not include holes rather the base portions may be directly tied to mesh fibres of the elongate body member 102 of the implant 100 flexibly so that the tip portions of the barbs 110 may move relative to the base portions. In an embodiment, the base portions may be tied with the implant fibres through knots. In an embodiment, the base portions of the barbs 110 may be fixed with the elongate body member 102 through adhesives. In an embodiment, the barbs 110 may be defined monolithically as integral structural portions of the elongate body member 102. In accordance with various other embodiments, the barbs 110 may be provided within the implant 100 through various other mechanisms and modes without any limitations.

In an embodiment, the barbs 110 are configured to assume one of the two states—an exposed state or a deployed state (hereafter used interchangeably without limitations), and an unexposed state or a relaxed state (hereafter used interchangeably without limitations). The barbs 110 may generally remain in the unexposed state and assume the exposed state upon activation during or after placement of the implant 100 inside a patient's body during a surgical treatment procedure. The unexposed state defines a state of the barbs 110 in which the barbs 110 substantially remain deployed on the outer surface of the implant 100 and do not extend outward from the outer surface. For example, in the unexposed state, longitudinal axes of the barbs 110 may be substantially parallel to longitudinal axis of the elongate body member 102 of the implant 100. In the unexposed state, the barbs 110 may lie on the outer surface of the elongate body member 102 on their own and no external force may be applied on the barbs 110 to change their positions with respect to the outer surface of the elongate body member 102. In the exposed state, the barbs 110 protrude outward from the outer surface of the implant 100 so that the longitudinal axes of the barbs 110 may no more be parallel to the longitudinal axis of the elongate body member 102 of the implant 100. When in the exposed state, in some embodiments, the longitudinal axes of the barbs 110 may define an angle with respect to the longitudinal axis of the elongate body member 102. The angle may be 90 degree or less than 90 degree based on fixation requirements. In some embodiments, the angle may be even more than 90 degree. An external force may be applied on the barbs 110 to change their positions and cause them to protrude outward and assume the exposed state. The exposed state may be defined by the change in the orientations of the barbs 110 when the external force is applied.

In an embodiment, the implant 100 includes a first flexible member 112 that couples with the first set of barbs 116 such that a portion of the first flexible member 112 extends beyond the proximal end portion 104 of the implant 100 and hangs outside the elongate body member 102 of the implant 100. The first flexible member 112 is coupled to the first set of barbs 116 such that upon stretching of the first flexible member 112, the first set of barbs 116 gets activated and assumes the exposed state. It must be appreciated that more than one such first flexible member 112 may be employed as is explained in accordance with some embodiments discussed in conjunction with later figures. In an example, the first flexible member 112 is attached to at least one barb of the first set of barbs 116. In an embodiment, the implant 100 includes a second flexible member 114 that couples with the second set of barbs 118 such that a portion of the second flexible member 114 extends beyond the distal end portion 106 of the implant 100 and hangs outside the elongate body member 102 of the implant 100. The second flexible member 114 is coupled to the second set of barbs 118 such that upon stretching or pulling the second flexible member 114, the second set of barbs 118 gets activated and assumes the exposed state. It must be appreciated that more than one such second flexible member 114 may be employed as is explained in accordance with some embodiments discussed in conjunction with later figures. In an example, the second flexible member 114 is attached to at least one barb of the second set of barbs 118. In some embodiments, the first and second flexible members 112 and 114 are sutures. In some embodiments, the first and second flexible members 112 and 114 are threads. In some embodiments, the first and second flexible members 112 and 114 are wires. In some embodiments, the first and second flexible members 112 and 114 are metallic strings. In some embodiments, the first and second flexible members 112 and 114 can be any other type of flexible element. In accordance with various embodiments, the barbs 110 may be configured to assume the exposed state through various activation and actuation mechanisms.

Figure 2:
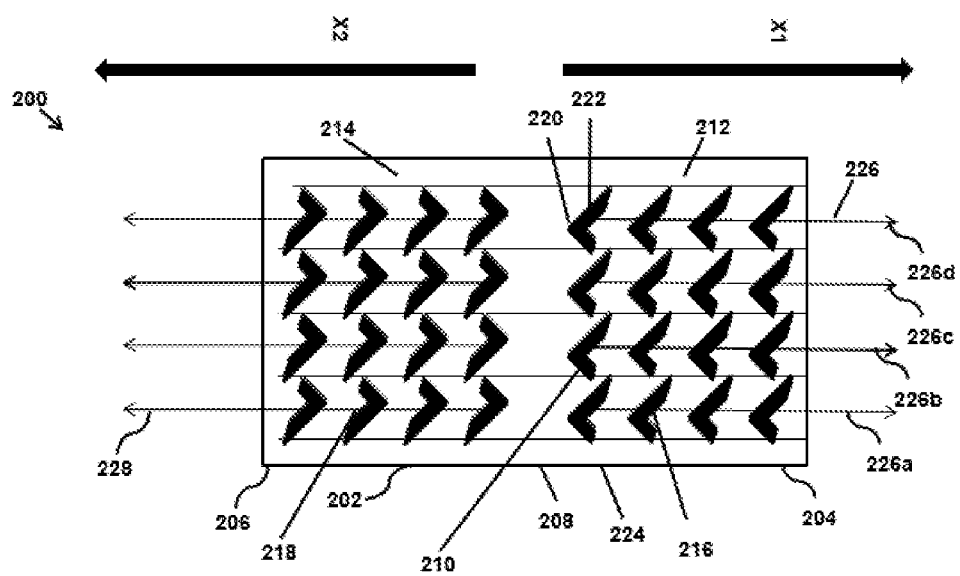
FIG. 2 illustrates a schematic diagram of an implant in accordance with an embodiment of the present invention.

FIG. 2 illustrates a schematic view of an implant 200 in accordance with an embodiment of the present invention.

The implant 200 includes an elongate body member 202. The elongate body member 202 includes a proximal end portion 204 and a distal end portion 206. The proximal end portion 204 and the distal end portion 206 of the implant 200 may be adapted to be fixed to bodily locations so as to support an organ or a weakened tissue. The implant 200 includes an intermediate portion 208 that may be positioned proximate the weakened tissue to be supported by the implant 200. For example, in an embodiment when the implant 200 is used for the treatment of urinary incontinence, the intermediate portion 208 also referred to as support portion 208 may be positioned underneath urethra for providing support to the urethra and the proximal end portion 204 and the distal end portion 206 may be attached to bodily tissues on either sides of the urethra to fix the implant 200 appropriately. The implant 200 can be defined with different shapes and sizes and may be fabricated from various materials such as those discussed in conjunction with FIG. 1 above without limitations.

The implant 200 includes a plurality of barbs 210 (hereafter interchangeably referred to as barbs 210) that are located at distinct locations on the implant 200. As shown, 32 such barbs are provided in the elongate body 202 member at 32 distinct locations. In accordance with the illustrated embodiment of FIG. 2, the barbs 210 are bi-directional in nature with one sided barbs disposed on a first portion 212 of the elongate body member 202 and substantially opposite sided barbs disposed on a second portion 214 of the elongate body member 202. For example, a first set of barbs 216 disposed on the first portion 212 of the elongate body member 202 may be directed toward a first direction and a second set of barbs 218 disposed on the second portion 214 of the elongate body member 202 may be directed toward a second direction. In some embodiments, orientations or directions of the barbs 210 may be defined based on fixation requirements such as discussed in conjunction with FIG. 1 without limitations.

Each of the barbs 210 includes a pointed tip portion 220 that is adapted to pierce bodily tissues for fixation. The barbs 210 include base portions such as a base portion 222 that extend from the elongate body member 202. In embodiments, the barbs 210 are configured on outer surface 224 of the elongate body member 202. In an embodiment, the barbs 210 are configured on the entire outer surface 224. In an embodiment, the barbs 210 are configured on a selected portion of the outer surface 224. The base portions 222 of the barbs 210 are coupled to the outer surface 224 of the elongate body member 202 so that the barbs 210 are movable with respect to the outer surface 224 of the elongate body member 202 in an embodiment. For example, the barbs 210 can rotate with respect to the outer surface 224. In an embodiment, the base portions 222 of the barbs 210 may include holes through which implant fibers may extend so as to couple the barbs 210 with the elongate body member 202 in a manner that would allow movement of the barbs 210 with respect to the outer surface 224 of the elongate body member 202. In an embodiment, the base portions 222 of the barbs 210 may not include holes rather the base portions 222 may be directly tied to mesh fibres of the elongate body member 202 of the implant 200 flexibly so that the tip portions 220 of the barbs 210 may move relative to the base portions 222. In an embodiment, the base portions 222 may be tied with the implant fibres through knots. In another embodiment, the base portions 222 of the barbs 210 may be fixed with the elongate body member 202 through adhesives. In another embodiment, the barbs 210 may be defined monolithically as integral structural portions of the elongate body member 202. In accordance with various other embodiments, the barbs 210 may be provided within the elongate body member 202 through various other mechanisms and modes without any limitations.

In an embodiment, the barbs 210 are configured to assume one of the two states—an exposed state or a deployed state (hereafter used interchangeably without limitations), and an unexposed state or a relaxed state (hereafter used interchangeably without limitations). These states are already discussed in conjunction with FIG. 1.

Figure 3:
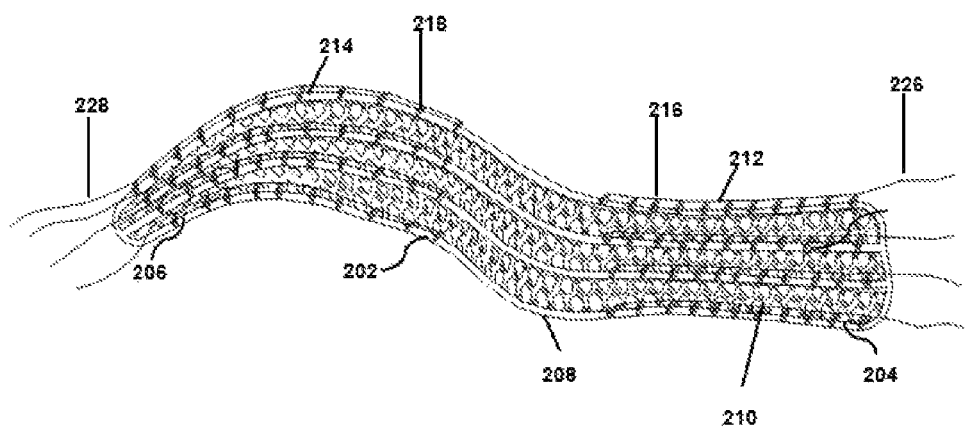
FIGS. 3 and 4 illustrate perspective diagrams of an implant in accordance with an embodiment of the present invention.
Figure 4:
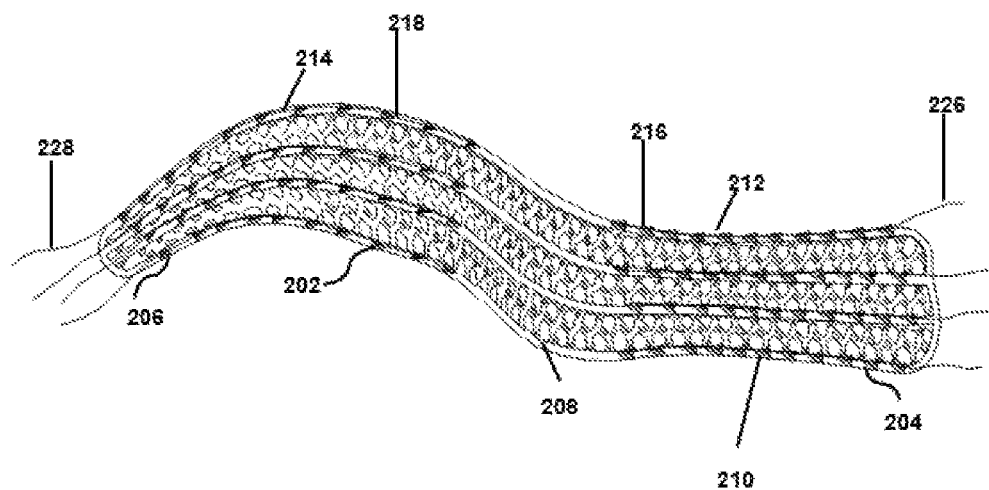

In an embodiment, the implant 200 includes a first set of flexible members 226 including four flexible members 226a, 226b, 226c, and 226d that couples with the first set of barbs 216 such that a portion of each of the four flexible members 226 extends beyond the proximal end portion 204 of the elongate body member 202 and hangs outside the elongate body member 202 of the implant 200. The first set of flexible members 226 are coupled to the first set of barbs 216 such that upon stretching or pulling of the first flexible members 226 along direction X1, the first set of barbs 216 gets activated and assumes the exposed state. In an example, the first flexible members 226 are attached to at least one barb. For example, as shown in FIG. 2, each of the first flexible members 226 is coupled to four barbs. In an embodiment, the implant 200 includes a second set of flexible members 228 that couples with the second set of barbs 218 such that a portion of each of the second flexible members 228 extends beyond the distal end portion 206 of the elongate body member 202 and hangs outside the elongate body member 202 of the implant 200. The second set of flexible members 228 (or second flexible members) is coupled to the second set of barbs 218 such that upon stretching or pulling the second flexible members 228 along direction X2, the second set of barbs 218 gets activated and assumes the exposed state. In an example, each of the second flexible members 228 is attached to at least one barb. For example, in the illustrated embodiment, each of the second flexible members 228 is coupled with four barbs. In some embodiments, the first and second flexible members 226 and 228 are sutures or threads or wires or metallic strings or any other type of flexible element. FIG. 3 illustrates a perspective view of the implant 200 of FIG. 2 with the barbs 210 in the exposed state. FIG. 4 illustrates a perspective view of the implant 200 of FIG. 2 with the barbs 210 in the deployed state.

Figure 5:
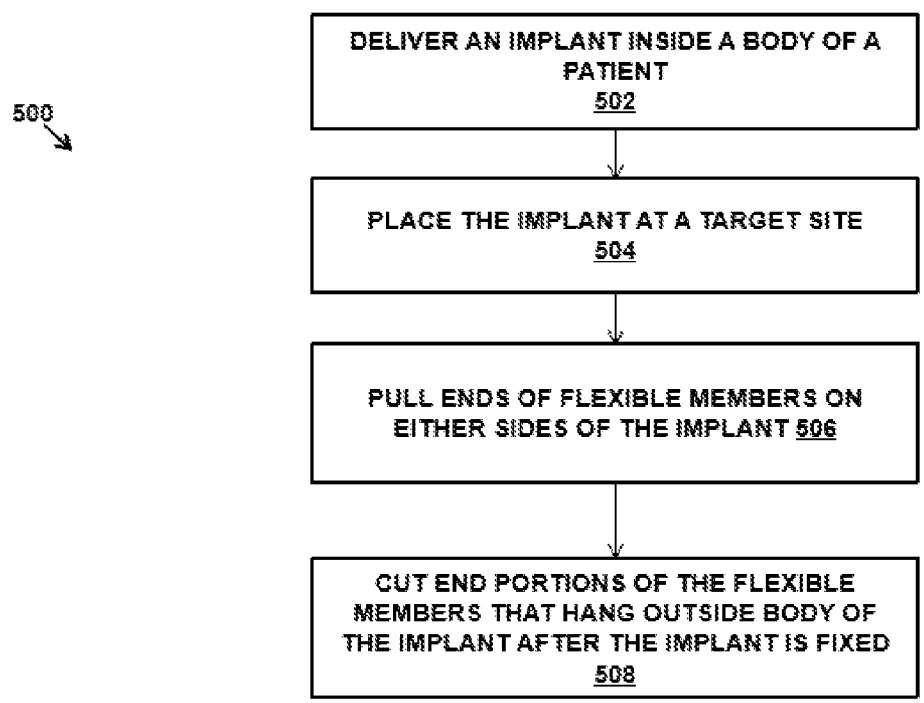
FIG. 5 illustrates a method diagram for delivering and fixing an implant inside a body of a patient in accordance with an embodiment of the present invention.

FIG. 5 illustrates a method diagram 500 for delivering and placing the implant such as 200 or 100 in accordance with an embodiment of the present invention. The method of delivering and placing the implant 200 is now described hereafter referring to FIGS. 5 and 2, 3, and 4 in an embodiment.

At step 502, the method 500 includes delivering the implant 200 inside a body of a patient. In some embodiments, the implant 200 is inserted inside the body through a laparoscopic approach. For example, the method 500 may include creating an abdominal incision for delivering the implant 200 inside the body laparoscopically. In some embodiments, the implant 200 is delivered through a transvaginal approach. The barbs 210 of the implant 200 may be in unexposed state during delivery and placing of the implant 200 at its target site. At step 504, the method 500 includes placing the implant 200 at the target site underneath the urethra or bladder neck so that the intermediate portion 208 of the elongate body member 202 supports the urethra and end portions 204 and 206 of the elongate member 202 along with the flexible members 226 and 228 extend out of the body through two contra lateral abdominal incisions. The method 500 further includes pulling ends of the flexible members 226 and 228 on either sides of the implant 200 through the two abdominal or other incisions at step 506. The pulling of the flexible members 226 and 228 causes the barbs 210 to get exposed and protrude outward causing to pierce surrounding bodily tissues. This fixes and secures the implant 200. At step 508, the method 500 may further include cutting the end portions of the flexible members 226 and 228 that hang outside the body after the implant 200 is fixed. The cut portions are then removed. Subsequently, bodily incisions may be closed after appropriate tensioning and fixation of the implant 200. The method 500 may include making two contra lateral abdominal incisions. The method 500 may further include making a vaginal incision.

Figure 6:
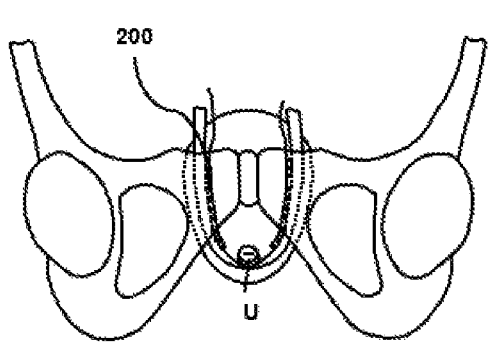
FIGS. 6-8 illustrate an implant positioned inside a body of a patient in accordance with an embodiment of the present invention.
Figure 7:
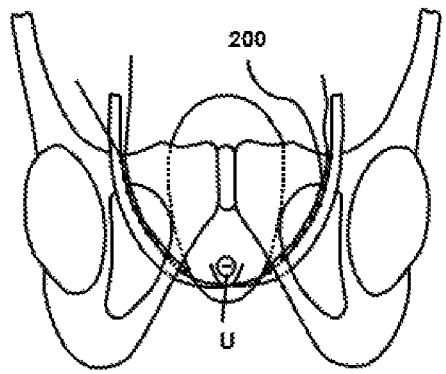

In some embodiments, the surgical procedure or method as discussed above may be employed to support the urethra U (shown in FIGS. 6, 7, and 8) for facilitating incontinence repair. In an embodiment, the procedure can be used to support the urethra U with the use of the implant 200 in a retro-pubic manner as shown in FIG. 6. FIG. 6 illustrates a front view of a pelvic bone of a female showing the position of the implant 200 supporting the urethra U with a retro-pubic passage of the implant 200. In an embodiment, the procedure as discussed above can be used to support the urethra U with the use of the implant 200 in a trans-obturator manner as shown in FIG. 7. FIG. 7 is a front view of a pelvic bone of a female showing the position of the implant 200 supporting the urethra U with a trans-obturator passage.

In an embodiment, the end portions 204 and 206 of the implant 200 may be coupled to dilators (not shown). For example, a first dilator may be coupled to the proximal end portion 204 and a second dilator may be coupled to the distal end portion 206 of the implant 200. The dilators are configured to be coupled to a surgical needle or a delivery device for facilitating delivery of the implant to the target site. In an embodiment, the implant 200 may be coupled to a sleeve (not shown) that covers the implant substantially. The sleeve may be removed after placement of the implant 200 at the target site and before letting the barbs 210 to expose. Once the sleeve is removed after placement, the flexible members 226 and 228 are pulled to cause the barbs 210 to be exposed. The sleeve facilitates in prevention of infection during the surgical procedure. In an embodiment, the sleeve may be coupled to the implant 200 through leader loops that may be fabricated from sutures or threads or any other flexible member. The sleeve may be decoupled from the implant by cutting and removing the leader loops.

Figure 8:
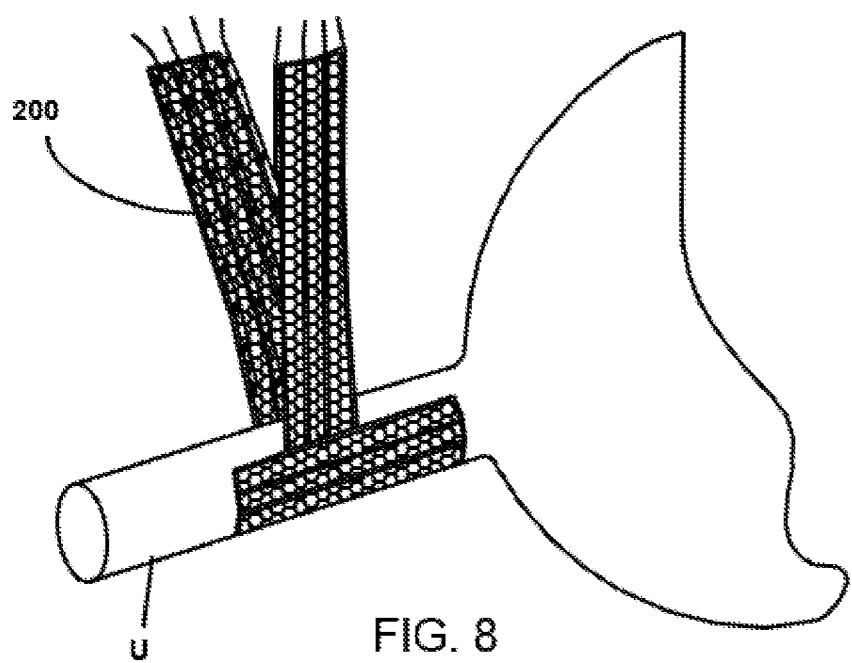

FIG. 8 is an enlarged view of the implant 200 supporting the urethra U in accordance with an embodiment of the present invention. As shown, the intermediate portion 208 of the implant 200 supports the urethra U and the end portions 204 and 206 of the implant 200 extend laterally from the urethra U and may me attached to surrounding bodily locations. In an embodiment, the barbs 210 are not provided on the intermediate portion 208 to avoid piercing of the urethra U by the barbs 210. The barbs 210 may be provided on the end portions 204 and 206 of the elongate member 202 so as to fix the implant 200 with the surrounding bodily locations without causing any damage to the urethra U, in an embodiment. The implant 200 and the barbs 210 may be manufactured from a suitable material so as to induce in-growth of fibroblastic cells which contribute to formation of scar tissue. Over time, the scar tissue matures and contractile forces within the scar tissue may cause a tightening and shrinking of the scar tissue. The scar formation takes place along full length of the implant 200 within the material of the implant 200. The scar formation and the material of the implant 200 creates a stiffening around and under the urethra U which then re-creates supporting function of original healthy tissue. Additionally, where the implant 200 is placed and tied laterally to the urethra U, support is added there as well. The inclusion of support below, to the sides and above the urethra U imparts a restriction and a compressive force upon the tissue of the urethra U which increases urethral sphincter opening pressure thereby reducing potential for involuntary urine loss.

Figures 9, 10:
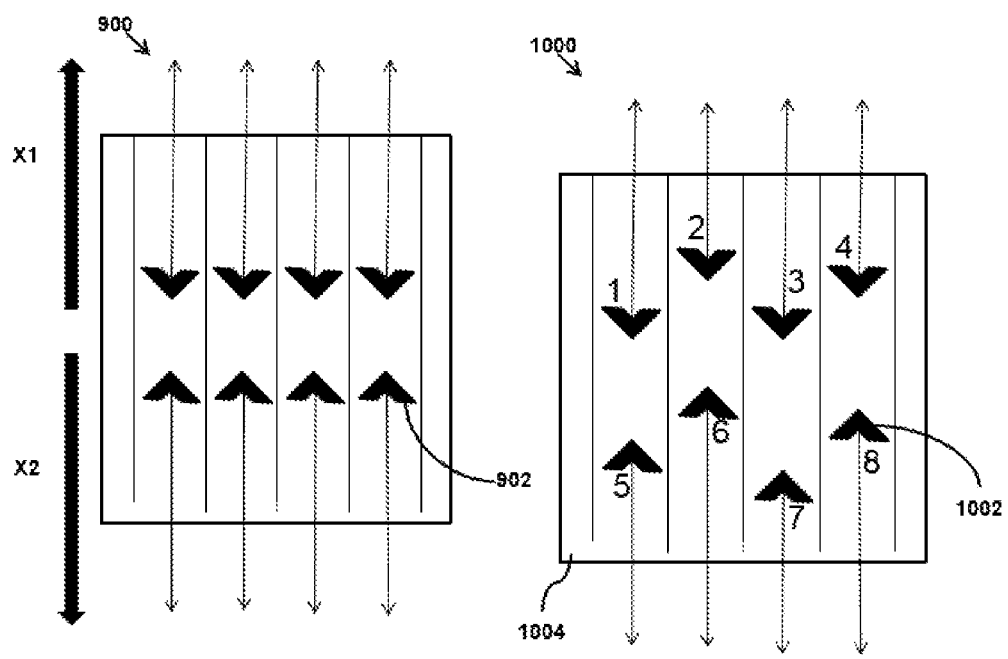
FIGS. 9-10 illustrate schematic diagrams of implants in accordance with embodiments of the present invention.

FIG. 9 illustrates an implant 900 in accordance with an embodiment of the present invention. FIG. 10 illustrates an implant 1000 in accordance with an embodiment of the present invention. The implant 900 of FIG. 9 and the implant 1000 of FIG. 10 are similar to the implant 200 except that numbers of barbs 902 and 1002 and locations of the barbs 902 and 1002 on the implants 900 and 1000 are different than the barbs 210 of implant 200. For example, FIG. 10 illustrates the barbs 1002 located at different selected locations on the elongate body member 1004 based on implant fixation requirements. For example, based on predefined calculations such as based on interaction of forces at different locations and based on several other factors, it is identified that implant fixation is required at locations 1, 2, 3, 4, 5, 6, 7, and 8 to provide an appropriate holding force and tension to the implant. Therefore, eight barbs 1002 are provided at these eight locations and each of these barbs 1002 is coupled to a respective flexible member similar to 226. Upon placement of the implant 1000 at the target site, the barbs 1002 are actuated and the implant 1000 is fixed in manners as discussed already above in conjunction with various figures.

The invention disclosed in accordance with the embodiments illustrated in conjunction with FIGS. 1-8 facilitate in fixation of the implant. The invention provides a way to avoid insertion of complex and bulky suturing and stapling devices to fix delicate tissues of and around urethra, bladder neck, vaginal walls, uterus etc which if punctured or damaged may result in heavy bleeding, infection, or even serious health issues. This can be at times life threatening. The invention avoids use of such bulky devices for suturing or fixation of the implant with bodily tissues. The implant may allow fixation to be performed easily in a simple manner with reduced chances of damage of tissues during fixation and delivery of the implant. The invention allows performing the surgical procedure quickly in a time efficient manner. The process of fixation can be made easier, time efficient, less invasive, and safe with the use of the disclosed invention.

Figure 11:
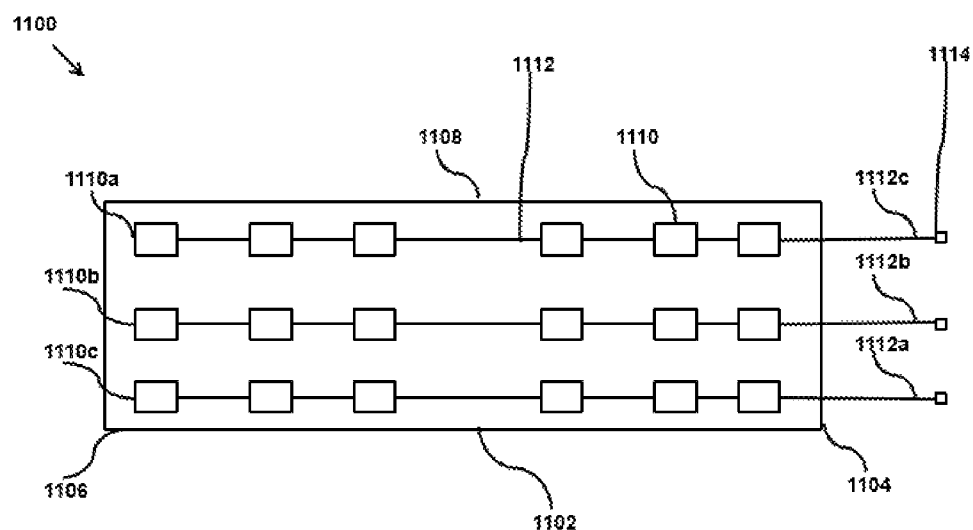
FIG. 11 illustrates a schematic diagram of an implant in accordance with an embodiment of the present invention.

FIG. 11 illustrates a schematic diagram of an implant 1100 for use in the treatment of stress urinary incontinence. In other embodiments, the implant 100 may be used for treatment of other pelvic floor disorders such as but not limited to anterior vaginal wall prolapse, posterior vaginal wall prolapse, apical prolapse, or any other organ or tissue prolapse. In some embodiments, the implant 1100 may be used to treat hernia. In other embodiments, the implant 1100 may be used to treat any other weakened organ or tissues in a patient's body.

The implant 1100 includes an elongate body member 1102. The elongate body member 1102 includes a proximal end portion 1104 and a distal end portion 1106. The proximal end portion 1104 and the distal end portion 1106 of the implant 1100 may be adapted to be fixed to bodily locations so as to support an organ or a weakened tissue. The implant 1100 includes an intermediate portion 1108 that may be positioned proximate the weakened tissue to be supported by the implant 1100. For example, in an embodiment when the implant 1100 is used for the treatment of urinary incontinence, the intermediate portion 1108 also referred to as support portion 1108 may be positioned underneath urethra for providing support to the urethra and the proximal end portion 1104 and the distal end portion 1106 may be attached to bodily tissues on either sides of the urethra to fix the implant 1100 appropriately. The implant 1100 may be defined for various shapes, sizes, and fabricated from a variety of materials such as those discussed in conjunction with FIG. 1.

The implant 1100 further includes a plurality of inflatable anchors 1110 that are located at distinct locations on the implant 1100. The inflatable anchors 1110 are positioned on an outer surface of the elongate body member 1102, in an embodiment. In an embodiment, the inflatable anchors 1110 are positioned on the proximal and distal end portions 1104 and 1106 of the implant 1100. In an embodiment, the inflatable anchors 1110 are positioned on the support portion or intermediate portion 1108 as well. The plurality of inflatable anchors 1110 are configured to assume an inflated state and a relaxed state (or a deflated state). In an embodiment, the plurality of inflatable anchors 1110 are configured to advance through bodily tissues upon inflation. In an embodiment, the plurality of inflatable anchors 1110 are fabricated from an expandable elastomeric material. In an embodiment, the expandable elastomeric material is bio-absorbable. In another embodiment, the expandable elastomeric material is not bio-absorbable. In an embodiment, the plurality of inflatable anchors 1110 are made of a natural material. In an embodiment, the plurality of inflatable anchors 1110 are made of a synthetic material. In some embodiments, the material of the plurality of inflatable anchors 1110 may be any biocompatible material. In an embodiment, the plurality of inflatable anchors 1110 are provided as projections or protuberances configured to assume the inflated state and the deflated state. In an embodiment, the plurality of inflatable anchors 1110 are provided as inflatable points along implant material that are configured to assume the inflated state and the deflated state.

The implant 1100 further includes a plurality of tubular members 1112a, 1112b, and 1112c together referred to as 1112 mechanically coupled to the plurality of inflatable anchors 1110. A first tubular member 1112a includes a lumen that provides a passageway for circulating a fluid through a first set of the plurality of inflatable anchors 1110a. In an embodiment, a second tubular member 1112b is also provided that is coupled to a second set of inflatable anchors 1110b. The second tubular member 1112b also includes a lumen that provides a passageway for circulating the fluid through the second set of anchors 1110b. In some embodiments, a third tubular member 1112c may be provided that is coupled to a third set of inflatable anchors 1110c. The third tubular member 1112c also includes a lumen that provides a passageway for circulating the fluid through the third set of anchors 1110c. In accordance with various embodiments, more than three or less than three such tubular members may be provided. In accordance with various embodiments, the number of inflatable anchors 1110 coupled to each such tubular member 1112 may vary. For example, the number of inflatable anchors 1110 provided with each tubular member 1112 may depend on tissue characteristics, implant characteristics, fixation strength requirements, length of the weakened tissue, and the like.

The implant 1100 may further include a plurality of injection ports 1114 coupled to the tubular members 1112 that may be configured for facilitating injection of the fluid through the inflatable anchors 1110. The injection ports 1114 may be removably coupled to the tubular members 1112. The injection ports 1114 may further be configured to receive an external injecting device (not shown) for injecting the fluid in the inflatable anchors 1110. Upon permanent fixation of the implant 1100, the end portions of the implant 1100 may be tied to bodily tissues and implant end portions extending beyond the bodily tissues including the injecting ports 1114 may be cut and thrown out thereby retaining the elongate body member 1102 of the implant 1100 only within the body for supporting the weakened tissues. In some embodiments, the implantable anchors 1110 may include pointed tip portions that are adapted to pierce bodily tissues for facilitating fixation when the inflatable anchors 1110 are inflated.

In an embodiment, the inflatable anchors 1110 are configured to assume one of the two states—the inflated state or deployed state or exposed state (hereafter used interchangeably without limitations), and the deflated state or relaxed state or unexposed state (hereafter used interchangeably without limitations). The anchors 1110 generally remain in the unexposed state and assume the inflated state upon inflation during or after placement of the implant 1100 inside a patient's body during a surgical treatment procedure. The unexposed state defines a state of the anchors 1110 in which the anchors 1110 substantially remain deployed on the outer surface of the implant 1100 and do not extend outward from the outer surface. In the exposed state, the anchors 1110 protrude outward from the outer surface of the implant 1100 upon inflation.

In an embodiment, the tubular members 1112 may extend from the proximal end portion 1104 to the distal end portion 1106 of the elongate body member 1102. The injection ports 1114 are provided at one of the end portions 1104 and 1106 such as at the proximal end portion 1104 as depicted in FIG. 11. In such embodiments, the fluid may be injected from the injection ports 1114 provided at the proximal end portion 1104 and the fluid is then carried through the tubular members 1112 to the plurality of inflatable anchors 1110 which are connected in series with the tubular members 1112. In some embodiments, as depicted in FIG. 11, the inflatable anchors 1110 on both sides of the intermediate portion 1108 are connected through same tubular members 1112. However, in some other embodiments, anchors provided on right side of the intermediate portion 1108 and anchors provided on left side of the intermediate portion 1108 may be coupled with different tubular members so that inflation and deflation of the inflatable anchors 1110 provided on either sides of the intermediate portion 1108 are controlled separately. In such embodiments, injecting ports such as the injecting ports 1114 are provided on both end portions 1104 and 1106 of the elongate body member 1102.

Figures 12, 13:
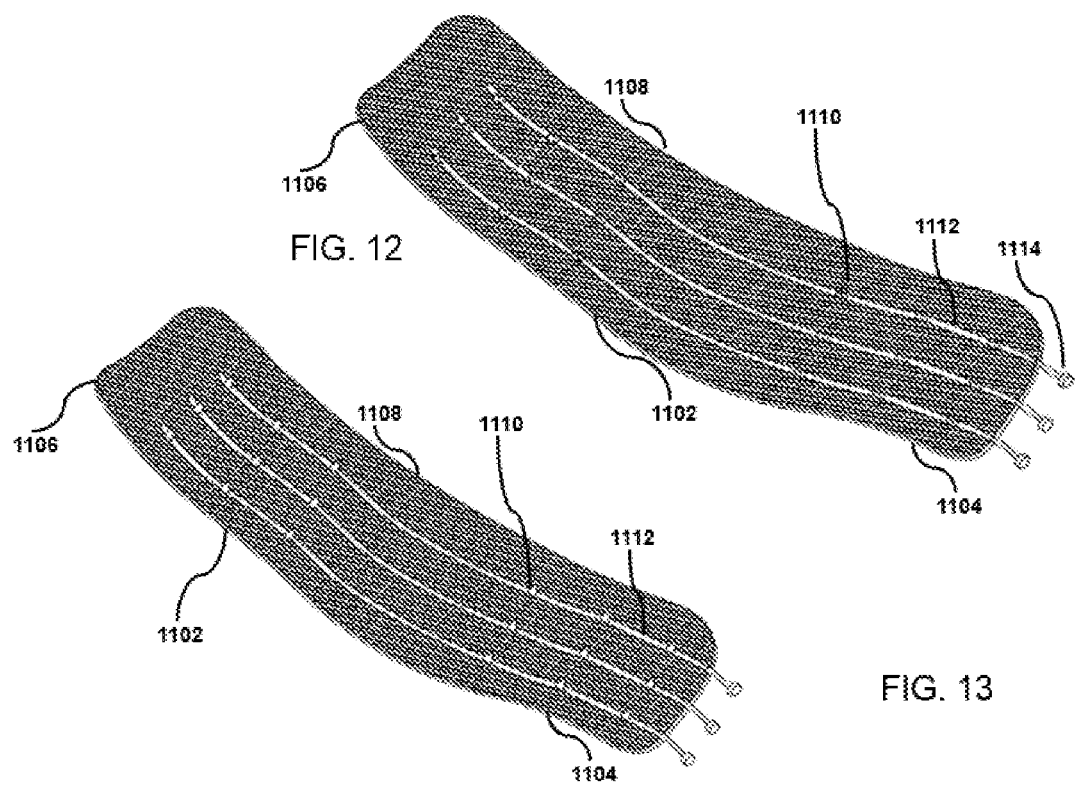
FIGS. 12-18 illustrate implants in accordance with different embodiment of the present invention.
Figures 14, 15:
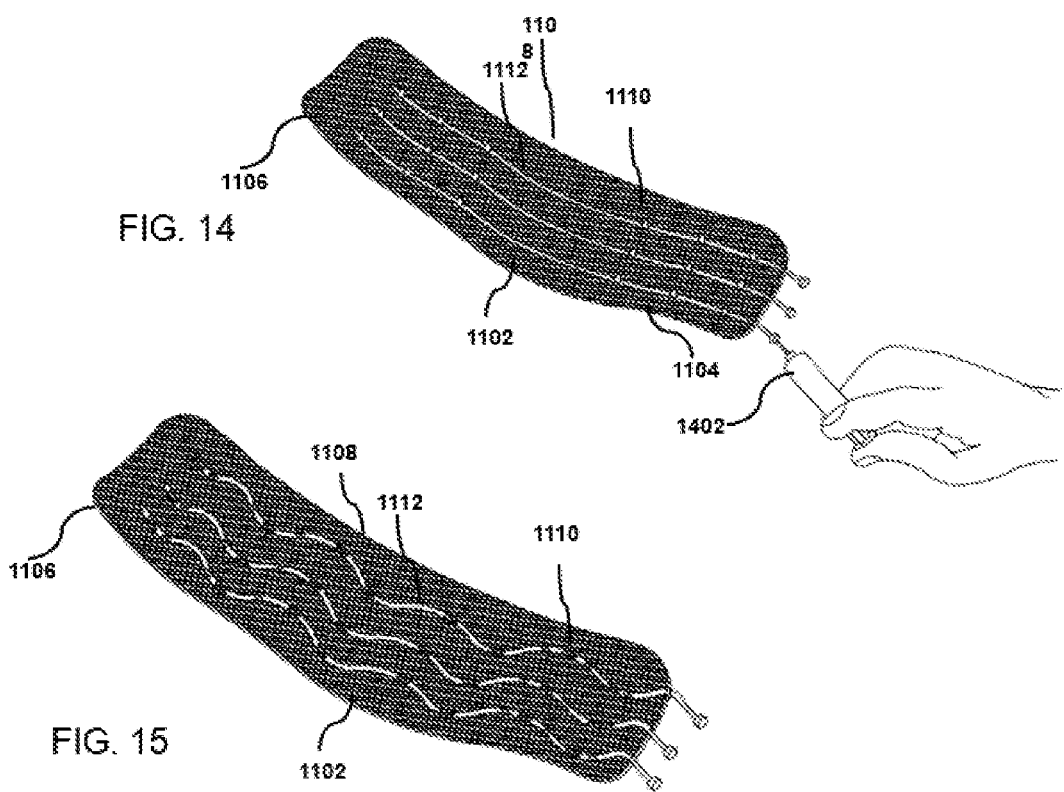
Figure 16:
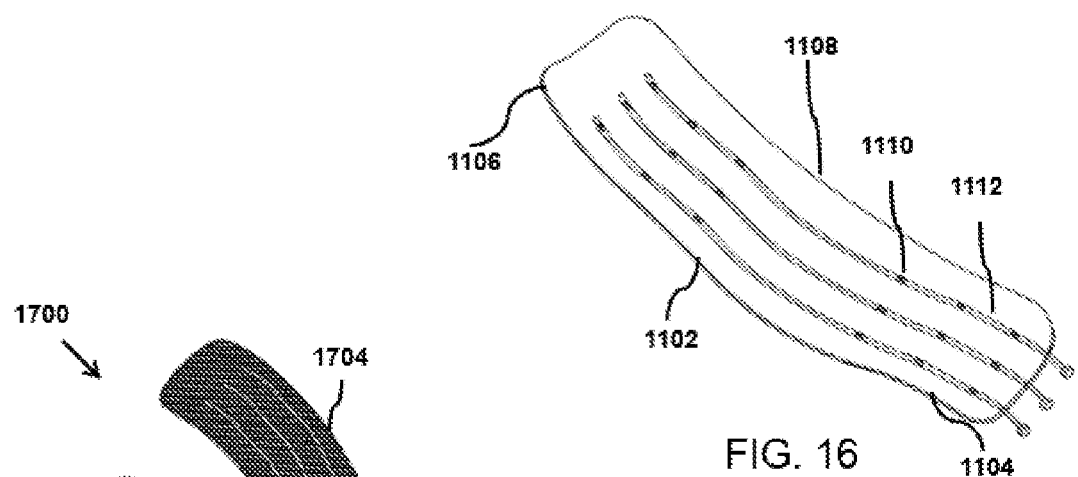

FIG. 12 illustrates a perspective view of the exemplary implant 1100 in accordance with an embodiment of the present invention with the inflatable anchors 1110 shown in the deflated state. FIG. 13 illustrates a perspective view of the exemplary implant 1100 with the inflatable anchors 1110 shown in the inflated state. As shown in FIG. 14, a fluid injection device 1402 may be coupled to an injection port of the implant 1100 so as to inject the fluid through the inflatable anchors 1110. FIG. 15 illustrates the implant 1100 in accordance with another embodiment of the present invention. As shown, the tubular member 1112 in accordance with this embodiment is flexible in nature. The tubular member 1112 may be wound over mesh fibres. The mesh fibres and the tubular members 1112 may be fabricated monolithically or may be coupled separately in accordance with various embodiments. In some embodiments, diameter of the tubular member 1112 may be of the order of diameter of mesh fibres. In some embodiments, the mesh fibres and the tubular member 1112 may be wound over one another. In an embodiment, as depicted in FIG. 16, the elongate body member 11102 is a non-mesh based strip as opposed to the mesh-based strip of implants discussed above in conjunction with FIGS. 2-10 and 12-15. The elongate body member 11102 may be fabricated from natural materials such as bodily tissues, cadaveric tissues, and the like. The elongate body member 1102 is defined in the form of a planar strip without mesh cells. The tubular member 1112 and the inflatable anchors 1110 may be fabricated monolithically and coupled to the elongate body member 1102. The coupling between the tubular member 1112 and the elongate body member 1102 may be provided through various means including such as welding, suturing, stapling, adhesive bonding, and the like.

Figure 17:
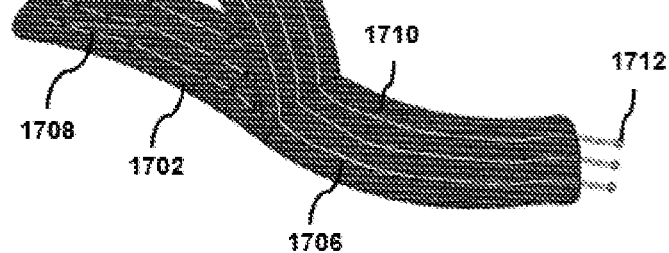

FIG. 17 illustrates an implant 1700 in accordance with another embodiment of the present invention. The implant 1700 includes a first strip 1702, a second strip 1704, and a third strip 1706. The first strip 1702, the second strip 1704, and the third strip 1706 are coupled together at a junction to define a Y-shaped implant. The Y-shaped implant 1700 is configured to provide support to vaginal walls for treatment of vaginal wall prolapse. The first strip 1702 is configured to be attached to an anterior vaginal wall. The second strip 1704 is configured to be attached to a posterior vaginal wall. The third strip 1706 is configured to be attached proximate sacrum of a patient. The implant 1700 further includes a plurality of inflatable anchors 1708. In an embodiment, each of the first strip 1702, the second strip 1704, and the third strip 1706 includes at least some of the plurality of inflatable anchors 1708. The implant 1700 further includes tubular members 1710 communicatively coupled to the inflatable anchors 1708. The tubular members 1710 and the inflatable anchors 1708 are similar to those discussed above in conjunction with various figures. The implant 1700 further includes injection ports 1712 attached to each of the tubular members 1710. In an embodiment, each of the three strips 1702, 1704, and 1706 may include the injection ports 1712 at their end portions. In another embodiment, only one or two strips may include the injection ports 1712 that may couple to the tubular members 1710 which carry the fluid to the inflatable anchors 1708 provided on each of the strips 1702, 1704, and 1706. In an embodiment, an injection device similar to those discussed above in conjunction with various figures (for example 1402) may be coupled to the injection ports 1712 for circulating fluid through the inflatable anchors 1708.

The invention discloses a method for delivering and placement of the implant 1100 in accordance with an embodiment of the present invention. The method includes delivering the implant 1100 inside a body of a patient. In some embodiments, the implant 1100 is inserted inside the patient's body through a laparoscopic approach. For example, the method may include creating an abdominal incision for delivering the implant 1100 inside the body laparoscopically. In some embodiments, the implant 1100 is delivered through a transvaginal approach. The inflatable anchors 1110 of the implant 1100 are in unexposed state during delivery and placement of the implant 1100 at its target site. The method includes placing the implant 1100 at a target site underneath the urethra so that the intermediate portion 1108 of the elongate body member 1102 supports the urethra and end portions 1104 and 1106 of the elongate member 1102 extend out of the body through two contra lateral abdominal incisions or groin incisions or at other locations. The method includes injecting the fluid through the tubular members 1112 mechanically coupled to the plurality of inflatable anchors 1110 so as to cause inflation of the inflatable anchors 1110, wherein the inflation facilitates fixation of the implant 1100 with bodily tissues.

The fluid injection device 1402 may be coupled to the injection ports 1114 of the implant 1100 so as to inject the fluid through the inflatable anchors 1100. The injection of the fluid causes the anchors 1110 to assume the inflated state thereby letting sharp tip portions of the anchors 1110 to pierce through bodily tissues. In case the implant 1100 needs to be adjusted, the method may further include withdrawing the fluid, after the inflatable anchors 1110 are affixed with the bodily tissues, for repositioning of the implant 1100. The withdrawal of the fluid causes the inflatable anchors 1110 to assume the relaxed state and get disassociated from the bodily tissues. The implant 1100 is then repositioned after the anchors 1110 are in relaxed sate. After repositioning, the method may further include injecting the fluid again through the tubular members 1112 so as to cause inflation of the inflatable anchors 1110, wherein the inflation fixes the implant 1100 with the bodily tissues again. The fluid may be withdrawn by creating a backward suction pressure through the injection device 1402 causing withdrawal of the fluid and deflation of the anchors 1110 which causes the disassociation of the anchors 1110 from the bodily tissues in an embodiment. In some embodiments, the tubular members 1112 and/or the inflatable anchors 1110 are provided with a valve arrangement that operates based on fluid pressure. The fluid injected inside the port remains within unless a backward suction pressure is created to withdraw the fluid outside from the inflatable anchors 1110. After some time, upon tissue ingrowth, the plurality of anchors 1110 may get engaged with the tissues and may not require any fluid therein to keep them maintained in the inflated state. In some embodiments, if the anchors 1110 are bioabsorbable, the anchors 1110 may get absorbed upon tissue ingrowth.

After the implant 1100 is properly positioned, affixed and tension is adjusted appropriately, the method may further include tying the end portions of the implant 1100 through sutures or staples with tissues. Any access portions of the elongate member 1102 are cut and removed. Subsequently, bodily incisions are closed. In some embodiments, the method may include making two contra lateral abdominal incisions. The method may further include making a vaginal incision. In some embodiment, the surgical procedure as discussed above for delivering the implant 1100 may be employed to support urethra in a manner as shown in FIGS. 6, 7, and 8 for facilitating incontinence treatment. In an embodiment, the procedure can be used to support the urethra U with the use of the implant 1100 in a retro-pubic manner as shown in FIG. 6. In an embodiment, the procedure as discussed above can be used to support the urethra U with the use of the implant 1100 in a trans-obturator manner as shown in FIG. 7.

In some embodiments, a method may be provided to place and fix the Y-shaped implant as discussed above in conjunction with FIG. 17 so as to support the vaginal walls through sacrocolpopexy or other vaginal wall repair procedures. The method may involve, delivering the implant 1700, attaching the first strip 1702 on the anterior vaginal wall, attaching the second strip 1704 on the posterior vaginal wall, and attaching the third strip 1706 proximate to the sacrum. The method may further include delivering the fluid so as to inflate the plurality of anchors 1708 that cause fixation of the implant 1700 with the vaginal walls.

In an example, the inflatable anchors such as 1110 may be provided at distinct locations on the outer surface of an approximately half of the length of the implant such as 1100 (or 1700 in an embodiment) including the proximal end portion 1104 and the distal end portion 1106. In an example, the inflatable anchors 1110 may be provided at distinct locations on the entire proximal end portion 1104 and the distal end portion 1106 which may define slightly lesser or slightly more than half of the length of the implant 1100. In an example, the inflatable anchors 1110 may be provided only on one side of the outer surface of the implant 1100 that comes in contact with the weakened tissue. In an example, the inflatable anchors 1110 may be provided with glue on tip portions of the inflatable anchors 1110 such that upon inflation when the inflatable anchors 1110 are caused to inflate and the tip portions come in contact with surrounding tissues, the glue comes in contact with the surrounding tissues and enhance attachment of the implant 1100.

The invention disclosed in accordance with the embodiments illustrated in conjunction with FIGS. 11-17 facilitate in fixation of the implant such as 1100. The invention provides a way to avoid insertion of complex and bulky suturing and stapling devices to fix delicate tissues of and around urethra, bladder neck, vaginal walls, uterus etc which if punctured or damaged may result in heavy bleeding, infection, or even serious health issues. This can be at times life threatening. The invention avoids use of such bulky devices for suturing or fixation of the implant 1100 with bodily tissues. The implant 1100 may allow fixation to be performed easily in a simple manner with reduced chances of damage to tissues during fixation and delivery of the implant 1100. The invention allows performing the surgical procedure quickly in a time efficient manner. The process of fixation can be made easier, time efficient, less invasive, and safe with the use of the disclosed invention. The invention allows repositioning and tension adjustment of the implant 1100 by inflating and deflating of the inflatable anchors if the implant 1100 is not positioned or tension is not provided as desired. By deflation that causes disengagement of the inflatable anchors from bodily tissues, the implant 1100 may be repositioned and/or tension may be readjusted and the inflatable anchors may be inflated again to provide engagement with the bodily tissues with better positioning and tension as needed.

Figure 18:
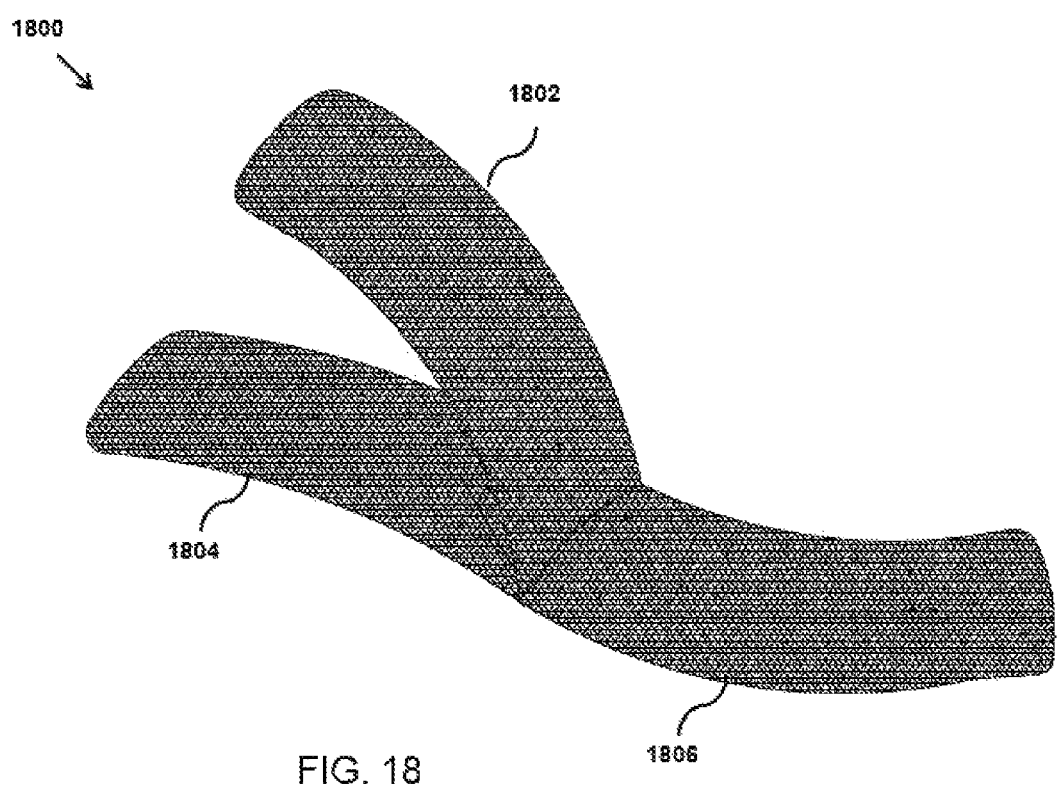

FIG. 18 illustrates a perspective view of an implant 1800 in accordance with an embodiment of the present invention. The implant 1800 includes a first portion 1802, a second portion 1804, and a third portion 1806. The three portions 1802, 1804, and 1806 can be defined rectangular or triangular or trapezoidal or curved in shape or may have any other shape. The first portion 1802 may be configured to be attached to a first bodily portion. In an embodiment, the first bodily portion may be an anterior vaginal wall such that the first portion 1802 may be configured to be positioned at the anterior vaginal wall. The second portion 1804 may be configured to be attached to a second bodily portion. In an embodiment, the second bodily portion may be a posterior vaginal wall such that the second portion 1804 may be configured to be positioned at the posterior vaginal wall. The third portion 1806 may be configured to be attached to a third bodily portion. In an embodiment, the third bodily portion may be sacrum or tissues proximate the sacrum or lumbar vertebra, tail bone, or illium portion of hip bone or uterus, or any other location or nearby tissues such that the third portion 1806 may be configured to be positioned at or proximate to the sacrum or lumbar vertebra, tail bone, and illium portion of hip bone or uterus or any other location or nearby tissues. In an embodiment, the implant 1800 can be configured as a Y-shaped mesh-based implant. In an embodiment, the implant 1800 can be fabricated from a natural tissue or material or from a synthetic material or a combination thereof. In an embodiment, the implant 1800 can be made as a mesh-based structure or non-mesh based planar structures. In an embodiment, the implant 1800 can be similar to the implants discussed in conjunction with various figures in the document above except that the implant 1800 may or may not include the inflatable anchors such as 1110 and plurality of barbs such as 110. In various embodiments, the implant 1800 can be made of various materials and can be defined for different shapes such as those discussed in conjunction with FIG. 1.

Figure 19:
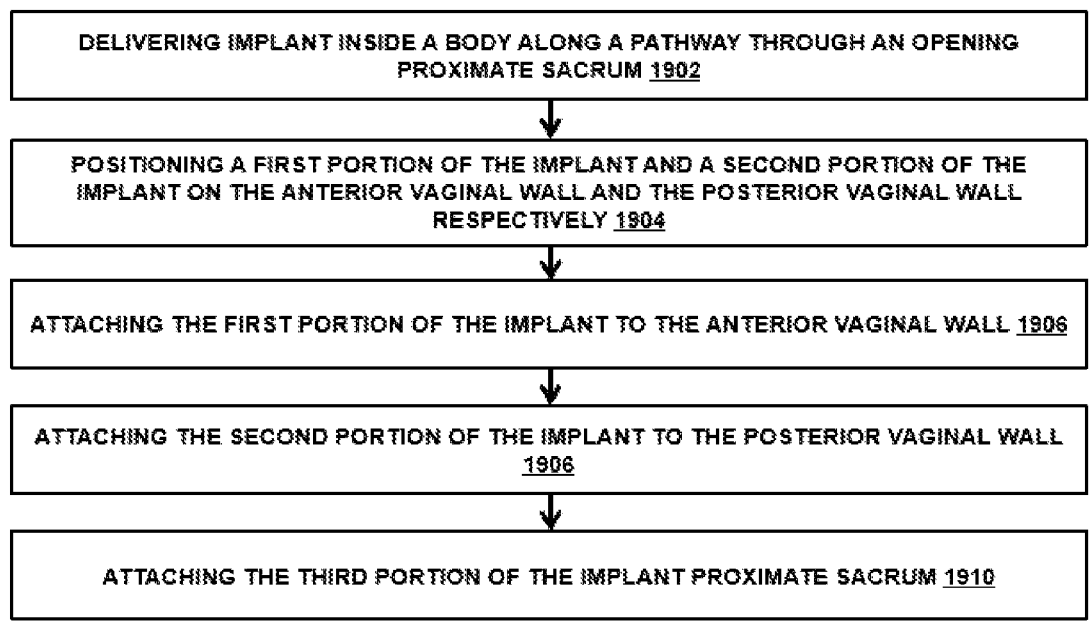
FIG. 19 illustrates a method diagram for performing a surgical procedure for delivering an implant in accordance with an embodiment of the present invention.

FIG. 19 illustrates a method diagram for repairing prolapsed tissues in accordance with an embodiment of the present invention. FIGS. 20A-20C illustrate schematic diagrams of delivery and placement of the implant 1800 in the body of the patient such as through the method of FIG. 19. The method is described herein in an embodiment referring to FIGS. 18, 19 and 20A-20C. In accordance with an embodiment, the method diagram specifically discusses repair of prolapsed vaginal walls such as an anterior vaginal and a posterior vaginal wall. However, in some embodiments, the method can be used to repair other prolapsed tissues without limitations.

At step 1902, the method includes delivering the implant 1800 inside a body along a pathway through an opening proximate sacrum S. Instead of using a vaginal or an abdominal incision for delivery and placing of the implant 1800, the implant 1800 may be inserted and placed along the pathway from an incision or cavity proximate the sacrum S extending through bodily tissues and reaching up to the prolapsed vaginal walls such as the anterior vaginal wall (AVW) and posterior vaginal wall (PVW) or other prolapsed tissues. In an embodiment, the opening can be a naturally existing lumen such as sacral foramen F. In an example, the sacral foramen F can be S1, S3 or any other foramen. In accordance with these embodiments, the implant 1800 may be inserted through the sacral foramen F so that incisions can be made to access the foramen F and allow placement of the implant 1800 proximate the prolapsed vaginal walls AVW and PVW by accessing the sacral foramen F.

In accordance with another embodiment, the opening can be an artificially created opening or cavity proximate a sacral foramen F such that the prolapsed tissue is accessed along the pathway through the artificially created cavity proximate the sacral foramen F. For example, in an embodiment, access to the prolapsed tissue may be made through or above the iliac bone such that an artificial lumen may be defined for example by drilling a hole to reach the prolapsed tissue. It is to be understood that the surgical approach may include other access passages (for reaching prolapsed vaginal or uterine tissue) in and around the sacrum S that is not categorically mentioned herein in various embodiments.

Once the implant 1800 is delivered inside the body proximate the vaginal walls AVW and PVW, the first portion 1802 of the implant 1800 and the second portion 1804 of the implant 1800 may be positioned on the anterior vaginal wall AVW and the posterior vaginal wall PVW respectively at appropriate locations where the first portion 1802 and the second portion 1804 are configured to be attached, at step 1904.

At step 1906, the method may include attaching the first portion 1802 of the implant 1800 to the anterior vaginal wall AVW. At step 1908, the method may include attaching the second portion 1804 of the implant 1800 to the posterior vaginal wall PVW. At step 1910, the method may include attaching the third portion of the implant 1800 to a tissue proximate the sacrum S. In an embodiment, the first portion 1802, the second portion 1804, and the third portion 1806 of the implant 1800 may be attached to the bodily tissues such as the anterior vaginal wall AVW, posterior vaginal wall PVW and the tissues proximate the sacrum S respectively with the use of staples, glues, sutures, anchors etc.

In accordance with an embodiment, the implant 1800 may be delivered inside the body with the use of a trocar or any other delivery tool. In an embodiment, the delivery tool may include a hollow construction to accommodate the mesh therein. The delivery tool may be configured to articulate or move to follow the path (i.e., above iliac bone, through the iliac bone or through the sacrum S or through the sacral foramen F) to reach the prolapsed vagina. For example, the delivery tool may be provided with a flexible and bendable construction to allow movement along the path. The implant 1800 may be removably coupled to the delivery tool prior to inserting the implant 1800 inside the body through the sacral foramina F or any other artificially created lumen or cavity around the sacrum S. The delivery tool may be inserted through the sacral foramina F or artificially created cavity by puncturing bodily tissues for defining the path for allowing the delivery tool to reach the prolapsed vagina or vaginal walls AVW and PVW. In an example, the delivery tool may be inserted with the help of an image guided technique so that the delivery tool and the path traversed by the delivery tool and the implant 1800 can be defined and monitored precisely without causing any injury to sacral nerves, other nerves or other locations etc. In operation, the delivery tool may be inserted along a selected path through the sacrum using the image guided technique to reach the prolapsed vagina. The indication that the delivery tool 1800 has passed the sacrum S to reach the prolapsed vagina can be made with the help of radiopaque markers provided on the delivery tool or radiopaque body of the delivery tool. Thereafter, the delivery tool may be allowed to contact a muscular layer of the prolapsed vagina for attachment of different portions of the implant at different locations as discussed above. In an embodiment, the prolapsed vagina may be coupled or tethered to the sacrum S or proximate tissues using a bioglue. A glue delivering facility may be provided in the delivery tool. For example, the delivery tool may include a barbed tip portion, a central lumen, and side holes. The delivery tool may include a glue container or may be adapted to be fed with a bioglue such that the bioglue can be injected out of the side holes. The position of the side holes of the delivery tool may be adjusted using the image guided technique prior to injecting the bioglue for attaching the implant 1800 at sacrum S or presacral space or proximate tissues. Finally, the bioglue may be injected out of the side holes into the presacral space or proximate tissues for fixing the prolapsed vagina to the sacrum S. Specifically, the bioglue coming out of the side holes of the delivery tool may form a connecting element or bridge that supports the prolapsed vagina (particularly the vaginal vault) with the sacrum S. Once the prolapsed vagina is fixed to the sacrum S, the delivery tool may be drawn out through the sacral foramen F.

In an example, a vaginal manipulator 2002 may be inserted through the vaginal lumen to push the vaginal vault near the sacrum S. This may facilitate in retaining the prolapsed vagina in correct anatomical position when the implant 1800 is deployed on the vaginal walls AVW and PVW. The vaginal manipulator 2002 may be used for adjusting and restoring a position of the vaginal vault or vaginal walls AVW and PVW. For example, the vaginal manipulator 2002 may be inserted through the vagina and thereafter the vaginal vault may be pushed towards the sacrum S for restoring and retaining the vaginal vault or vaginal walls AVW and PVW in the correct anatomical position. The vaginal vault may be thereafter coupled or tethered to the sacrum S for supporting the prolapsed vagina and vaginal walls AVW and PVW when restored in its correct anatomical position. The vaginal manipulator 2002 may be radiopaque in nature so that a relative position of the manipulator 2002 and the delivery tool 2100 can be determined in real-time with the help of image guiding technique when the implant 1800 is deployed.

The disclosed method for correcting pelvic organ prolapse is a minimally invasive procedure. Specifically, the disclosed method precludes a need for large or multiple abdominal incisions or vaginal incisions unlike conventional sacrocolpopexy procedure in which such incisions are used for accessing the prolapsed tissue. Also, a patient undergoing such procedure may experience a less traumatic, scar free, speedy recovery, and less expensive procedure. Also, since there are no vaginal incisions, therefore, vaginal wall erosions of the implant 1800 can be prevented.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. An implant for treatment of stress urinary incontinence, the implant comprising:
    an elongate body member with a proximal portion, a distal portion, and an intermediate portion, wherein the intermediate portion is configured to be positioned proximate a weakened tissue underneath urethra to provide support;
    a plurality of bi-directional barbs positioned on an outer surface of the elongate body member, the plurality of barbs including a first set of barbs directed to a first direction and disposed proximate the proximal portion wherein the first set of barbs are disposed in a series of at least two rows with each row containing at least four barbs and a second set of barbs directed to a second direction and disposed proximate the distal portion wherein the second set of barbs are disposed in a series of at least two rows with each row containing at least four barbs, wherein the plurality of barbs are configured to assume an exposed state and a relaxed state;
    a plurality of first flexible members, wherein each of the plurality of first flexible members is attached to the at least four barbs of a row of the first set of barbs, and a plurality of second flexible members, wherein each of the plurality of second flexible members is attached to the at least four barbs of a row of the second set of barbs such that each row of the at least four barbs is activated through a different flexible member of the plurality of first flexible members and the plurality of second flexible members, wherein the plurality of first flexible members and the plurality of second flexible members are configured to cause the first set of barbs and the second set of barbs respectively to assume the exposed state from the relaxed state upon activation such that the activation is configured to cause anchoring of exposed barbs into soft tissues during a surgical implant of the implant.

2. The implant of claim 1, wherein each of the plurality of barbs include a base portion and a sharp tip portion, the sharp tip portion configured to pierce the soft tissues for fixation of the implant.

3. The implant of claim 2, wherein the sharp tip portion defines a curved shape that is configured to engage with the soft tissues once a barb is in the exposed state.

4. The implant of claim 1, wherein each of the plurality of barbs include a slot for associating a respective flexible member with a barb.

5. The implant of claim 1, wherein in the exposed state, the plurality of barbs protrudes outward from an outer surface of the elongate body member.

6. The implant of claim 1, wherein the plurality of barbs are biased to remain in the relaxed state and assume the exposed state upon activation after placement of the implant at a target site.

* * * * *